United States Patent [19]

Kreutzer et al.

[11] Patent Number: 4,636,507

[45] Date of Patent: Jan. 13, 1987

[54] HOST DEFENSE MECHANISM ENHANCEMENT

[75] Inventors: Donald L. Kreutzer, Avon, Conn.; William J. Novick, Jr., Lebanon, N.J.; Michael P. Sheetz, Avon, Conn.

[73] Assignee: Hoechst-Roussel Pharmaceuticals Inc., Somerville, N.J.

[21] Appl. No.: 605,085

[22] Filed: Apr. 30, 1984

[51] Int. Cl.$^4$ ............................................. A61K 31/52
[52] U.S. Cl. .................................................. 514/263
[58] Field of Search ....................................... 514/263

[56] References Cited

U.S. PATENT DOCUMENTS

| | | | |
|---|---|---|---|
| 2,994,640 | 8/1961 | Zellner et al. | 514/263 |
| 3,422,107 | 1/1969 | Mohler et al. | |
| 3,737,433 | 6/1973 | Mohler et al. | 514/929 |
| 4,089,959 | 5/1978 | Diamond | 514/263 |
| 4,189,469 | 2/1980 | Gleixmer et al. | |
| 4,360,522 | 11/1982 | Schaeffer | 514/263 |

FOREIGN PATENT DOCUMENTS 803051  7/1975  Belgium .

OTHER PUBLICATIONS

S. Hayashi et al., *Chemical and Pharmaceutical Bulletin*, vol. 26, p. 1384 (1976).
K. Fujimoto et al., *Chemical and Pharmaceutical Bulletin*, vol. 24, p. 1137 (1976).
M. P. Sheetz et al., in "White Cell Mechanics: Basic Science and Clinical Aspects," H. J. Meiselman, M. A. Lichtman and P. L. LaCelle, Editors, Kroc Foundation Series, vol. 16, A. R. Liss, Inc., New York, NY 1984, pp. 87 to 94.
R. D. Stevenson et al., *Clinical and Experimental Immunology*, vol. 33, p. 478 (1978).
R. L. Tse et al., *Journal of Laboratory Clinical Medicine*, vol. 80, p. 265, (1972).
B. F. Debske et al., *Biochemical and Biophysical Research Communications*, vol. 108, p. 1228 (1982).
P. Phelps and D. Stanislaw, *Arthritis and Rheumatism*, vol. 12, p. 181, (1969).
D. A. Deporter, *British Jounal of Pharmacology*, vol. 60, p. 205 (1977).
D. L. Kreutzer et al., *Immunopharmacology*, vol. 1, p. 39 (1978).
H. J. Hinze, *Arzneimittel-Forschung*, vol. 22, p. 1492 (1972).
G. W. Sullivan et al., *Clinical Research*, vol. 32, p. 559A (1984).

*Primary Examiner*—Sam Rosen
*Attorney, Agent, or Firm*—Raymond R. Wittekind

[57] ABSTRACT

A method of enhancing host defense mechanisms utilizing xanthines is disclosed.

53 Claims, No Drawings

HOST DEFENSE MECHANISM ENHANCEMENT

INTRODUCTION

The present invention relates to a method of enhancing host defense mechanisms against trauma. More particularly, the present invention relates to a method of enhancing host defense mechanisms against trauma involving administering to a host in need of defense mechanism enhancement a compound of the formula

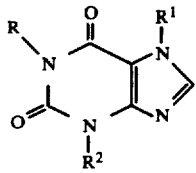

wherein R and $R^1$ are the same or different and are lower alkyl,

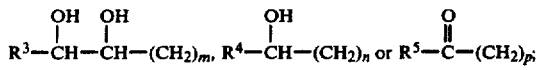

$R^3$ and $R^4$ are the same or different and are hydrogen or lower alkyl; $R^5$ is lower alkyl; and m, n and p are the same or different and are 2, 3 or 4, with the proviso that R, $R^1$, and $R^2$ are not simultaneously lower alkyl, or a pharmaceutically acceptable acid addition salt thereof.

BACKGROUND OF THE INVENTION

A mechanism by which a host defends against trauma involves leukocytic infiltration followed by phagocytosis. In the infiltration process, leukocytes present in circulating blood stick to blood vessel walls, emigrate through the wall (diapedesis), and migrate to the site of the trauma. The migration may be random or directional. Directional migration is termed "chemotaxis". In the phagocytotic (cellular eating) process, leukocytes attach to foreign matter at the traumatic site, engulf and injest it and, finally, kill and digest the offensive bodies. In so doing, leukocytes destroy matter associated with the trauma, cleanse the traumatic site, and provide future protection against trauma. Agents which increase the motility of leukocytes from the circulation to the site of the traumatic attack would thus enhance the host's ability to defend against such attack. We have now have found that xanthines promote leukocytic locomotion, thereby enhancing the host's defense mechanisms.

DESCRIPTION OF THE INVENTION

The present invention relates to a method of enhancing host defense mechanisms against trauma which comprises administering to a host in need of defense mechanism enhancement a defense mechanism enhancing effective amount of a xanthine of the formula

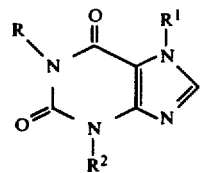

wherein R and $R^1$ are the same or different and are lower alkyl,

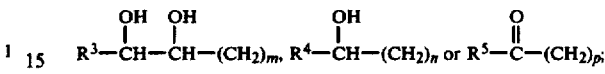

$R^3$ and $R^4$ are the same of different and are hydrogen or lower alkyl; $R^5$ is lower alkyl; and m, n and p are the same or different and are 2, 3, or 4, with the proviso that R, $R^1$ and $R^2$ are not simultaneously lower alkyl, or a pharmaceutically acceptable acid addition salt thereof.

Prefered xanthines are those wherein:

a.
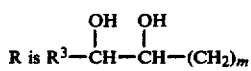

wherein $R^3$ and m are as hereinbeforedefined;

b.
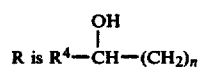

wherein $R^4$ and n are as hereinbeforedefined;

c.
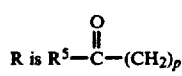

wherein $R^5$ and p are as hereinbeforedefined;

d.
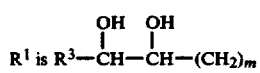

wherein $R^3$ is as hereinbeforedefined;

e.
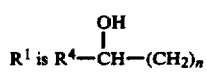

wherein $R^4$ and n are as hereinbeforedefined; and f.
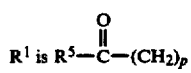

wherein $R^5$ and p are as hereinbeforedefined.

Most prefered are xanthines wherein R is

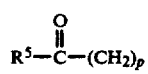

wherein $R^5$ and p are as hereinbeforedefined.

As used throughout the specification and appended claims, the term "alkyl" refers to a straight or branched chain hydrocarbon containing no unsaturation and having 1 to 8 carbon atoms such as methyl, ethyl, 1-propyl, 2-propyl, 1-butyl, 2-pentyl, 3-hexyl, 4-heptyl, 2-octyl and the like. The term "lower" as applied to the aforementioned moieties refers to a group having 1 to 6 carbon atoms.

The xanthines of the method of the present invention characterized by the presence of oxoalkyl group at the 3- and/or 7-position of the ring system, i.e., the compounds of formula 1 wherein R and $R^1$ are

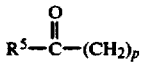

wherein $R^5$ and p are as hereinbeforedescribed, and hydroxyalkyl at the same positions, i.e., compounds of formula 1 wherein R and $R^1$ are

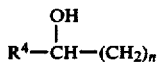

wherein $R^4$ and n are as hereinbeforedescribed, are disclosed in U.S. Pat. No. 3,737,433, issued June 5, 1973, and Belgium Patent No. 831,051, granted Nov. 3, 1975, respectively. The aforementioned xanthines are prepared by the processes described therein, or processes similar thereto.

The xanthines of the method of the present invention characterized by the presence of a dihydroxyalkyl group at the 3- and/or 7-positions, i.e., compounds of formula 1 wherein R and $R^1$ are

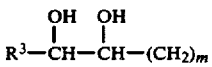

wherein $R^3$ and m are as hereinbeforedefined, are described in W. Mohler, et al., Arch. Pharm., 299,448(1966). The aforesaid xanthines are prepared by the processes described therein, or processes similar thereto.

Administration of the hereinbeforedescribed xanthines to a host such as a mammal, for example, a mouse or rabbit, or a fish or avian species, increases the motility, random and directional of leukocytes to the traumatic site, at which site the leukocyte destroy the offensive matter, cleanse the site, and provide future protection.

As used herein, i.e., throughout the specification and appended claims, the term "trauma" refers broadly to cellular attack by foreign bodies and physical injury of cells. Included among foreign bodies are microorganisms, particulate matter, chemical agents, and the like. Included among physical injuries are, mechanical injuries such as abrasions, lacerations, contusions, wounds, and the like, thermal injuries such as those resulting from excessive heat or cold, electrical injuries such as those caused by contact with sources of electrical potential, and radiation damage caused, for example, by prolonged, intensive exposure to infrared, ultraviolet or ionizing radiation.

Microorganisms comprise bacilli, fungi and yeast, viruses, parasites, and the like. Representative bacilli are:

a. Actinomyces spp.;
b. Bacteroides spp.;
c. Corynebacterium spp.;
d. Enterobacteriacea;
e. Enterococcus;
f. Haemophilus spp.;
g. Micrococcus spp.;
h. Neissera spp.;
i. Staphylococcus aureus;
j. S. epidermidis;
k. Streptococcus pneumoniae;
l. Clostridium spp.;
m. Streptococcus agalactiae;
n. Bacillus spp.;
o. H. influenzae;
p. Moraxella spp.;
q. Mycobacteria spp.;
r. Pseutodomonas aeruginosa;
s. Vibrio spp.; and
t. Mycoplasma.

Representative fungi and yeast are:
a. Microspurum;
b. Blastomyces;
c. Histoplasma;
d. Aspergillus;
e. Cryptococcus;
f. Candida;
g. Coccidioides; and
h. Candida albicans.

Representative viruses are:
a. Rhinovirus;
b. Parainfluenza;
c. Enterovirus;
d. Influenza;
e. Chlamydiae;
f. Smallpox and vaccinia;
g. Herpes simplex;
h. Measles;
i. Rubella;
j. Arbovirus (Western, Eastern and Venezuelan equine encephalitis, and California encephalitis);
k. Rabies;
l. Colorado tick fever;
m. Yellow fever;
n. Dengue;
o. Virus B (HB Ag); and
p. Virus A (HAV).

Representative parasites are:
a. Trypanosoma cruzi;
b. Entamoeba histolytica;
c. Leishmania brasiliensis;
d. Leishmania tropica;
e. Leishmania donovani;
f. Toxiplasma gondii;
g. Plasmodium falciparum;
h. Trypanosoma rhodesiense;
i. Lia loa;
j. Trichomonas hominis;
k. Schistosoma japonicum;
l. Schistosoma mansoni; and
m. Fasciola hepatica.

Particulates include silica, asbestos, monosodium urate, cotton fibers, coal dust, beryllium, and the like.

Chemical agents include heavy metals such as lead, chromium, mercury, arsenic, and the like, organic solvents such as trichloroethylene, and the like, herbicides such as trichlorophenoxyacetic acid and the like, and pesticides such as mirex and the like.

Comprehended among leukocytes, i.e., white blood cells, are granulocytic cells such as the polymorphonuclear neutrophils, basophils and eosinophils, monocytes such as the mononuclear macrophages, and lymphocytes, for example, B- and T- lymphocytes.

The chemotactic effect of the xanthines describeherein, the change in the directional motility of leukocytes, is demonstrated by a modification of the Boyden technique described by P. A. Ward and C. G. Cochrane, J. Exp. Med., 121, 215 (1965). In this assay rabbit polymorphonuclear leukocytes (PMNs) were isolated by lavage from the peritoneum of rabbits 4 to 8 hours after interperitoneal injections of 200 mls of 0.1% glycogen in saline solution. The PMNs were washed at least once in Hanks balanced salt solution (HBSS) and resuspended at a final concentration of $2 \times 10^6$ cells/ml in HBSS containing 0.1% Bovine serum albumin. To develop a standard chemotatic factor curve, the synthetic tripeptide formyl-met-leu-phe was prepared in serial dilutions from $10^{-6}$M to $10^{-13}$M in HBSS, and aliquots of each concentration of formyl-met-leu-phe were placed in the bottom of a standard chemotaxis chamber. Next a milapore chemotaxis membrane (0.8-3.0u pure size) was added and the chamber was assembled. Indicator PMNs were then placed in the top of the hemotatic chamber, and the entire apparatus was incubated for 60 to 90 minutes at 37° C. After incubation, the membranes were removed, organized within a staining rack, and the membranes were stained with hemotoxylin and clarified with oil. Next, the membranes were fixed to slides and evaluated for chemotatic responsiveness. The evaluation of chemotactic responsiveness was done directly under a microscope at 400× magnification. Special effort is undertaken to develop a consistent monolayer evaluation in which a consistent number of cells on the monolayer was counted. The cell number at each 10 um level underneath the monolayer was counted and the chemotactic index (C.I.) was calculated by (1) multiplying individual count by their corresponding depth of penetration, and (2) summing the totals for any individual fields and membranes. In general, all assays are done using triplicate membranes at each test concentration and at least 3 to 5 high powered fields were counted per membrane. Utilizing this procedure, a basic evaluation of cell migration in a chemotaxis chamber can be done and a standard dose response curve for formyl-met-leu-phe can be generated and a maximum chemotactic response for formyl-met-leu-phe can be generated and a maximum chemotactic response for formyl-met-leu-phe obtained.

To test the effect of various xanthines on the chemotactic response of rabbit PMNs to formyl-met-leu-phe a standard final concentration of test xanthine (0.02 mg/ml) and formyl-met-leu-phe ($10^{-9}$M) were added to the bottom of a chemotaxis chamber and the membrane and PMNs were added as described above. Positive controls of $10^{-9}$M formyl-met-leu-phe only and HBSS only (negative control) were also included in our chemotaxis analysis. The chemotactic chambers were then incubated for 60-90 minutes at 37° C. The resulting chemotactic membranes were processed and the Chemotactic Index determined as described above. To compare the effect of the various xanthine compounds on formyl-met-leu-phe induced chemotaxis, all data was expressed as percent positive control (formyl-met-leu-phe only) using the following equation:

$$\frac{\text{C.I. of Test Xanthine + formyl-met—leu—phe}}{\text{C.I of formyl-met—leu—phe only}} \times 100$$

% formyl-met—leu—phe Positive Control

The normal range of formyl-met-leu-phe only response was 100%±10%. Thus any xanthine compound that induced greater than 110% response when incubated as described was considered to significantly enhance the of response to the formyl-met-leu-phe.

RESULTS

| Compound | Chemotactic Activity (% Positive Control) |
|---|---|
| 1-(3,4-dihydroxybutyl)-3-methyl-7-(1-butyl)xanthine | 195 |
| 1-(4,5-dihydroxypentyl)-3-methyl-7-(1-propyl)xanthine | 135 |
| 1-(5,6-dihydroxyhexyl)-3-methyl-(1-propyl)xanthine | 168 |
| 3,7-dimethyl-1-(5-hydroxyhexyl)xanthine | 175 |
| 1-(5-hydroxyhexyl)-3-methylxanthine | 120 |
| 3,7-diethyl-1-(5-hydroxyhexyl)xanthine | 130 |
| 3-methyl-1-(5-oxohexyl)-7-(1-propyl)xanthine | 128 |
| 7-ethyl-3-methyl-1-(5-oxohexyl)xanthine | 111 |
| 7-(1-butyl)-3-methyl-1-(5-oxohexyl)xanthine | 115 |
| 3-methyl-1-(4-oxopentyl)-7-(1-propyl)xanthine | 145 |
| 3,7-diethyl-1-(5-oxohexyl)xanthine | 110 |
| 3,7-dimethyl-1-(5-oxohexyl)xanthine | 155 |
| 7-(3,4-dihydroxybutyl)-1,3-diethyl)xanthine | 123 |
| 1-(1-butyl)-7-(5,6-dihydroxyhexyl)-3-methylxanthine | 140 |
| 1,3-diethyl-7-(5,6-dihydroxyhexyl)xanthine | 132 |
| 7-(5-hydroxyhexyl)-3-methyl-1-(1-propyl)xanthine | 125 |
| 1-ethyl-3-methyl-7-(5-oxohexyl)xanthine | 114 |

Chemotactic activity is achieved when the xanthines are administered to a subject requiring such treatment as an effective oral, parenteral or intravenous dose of from 0.10 to 10.0 mg/kg of body weight per day. A particularly prefered effective amount is about 1.0 mg/kg of body weight per day. It is to be understood, however, that for any particular subject, specific dosage regimens should be adjusted to the individual need and the professional judgment of the person administering or supervising the administration of the aforesaid compound. It is to be further understood that the dosages set forth herein are exemplary only and they do not, to any extent, limit the scope or practice of the invention.

Effective amounts of the xanthines may be administered to a subject by any one of various methods, for example, orally as in capsule or tablets, or parenterally in the form of sterile solutions. The xanthines, while effective themselves, may be formulated and administered in the form of their pharmaceutically acceptable addition salts for purposes of stability, convenience of crystallization, increased solubility and the like.

Prefered pharmaceutically acceptable addition salts include salts of mineral acids, for example, hydrochloric acid, sulfuric acid, nitric acid and the like, salts of monobasic carboxylic acids such as, for example, acetic acid, propionic acid and the like, salts of dibasic carboxylic acids such as, for example, maleic acid, fumaric acid, oxalic acid and the like, and salts of tribasic carboxylic acids such as, for example, carboxysuccinic acid, citric acid and the like.

The xanthines may be administered orally, for example, with an inert diluent or with an edible carrier. They may be enclosed in gelatin capsules or compressed into tablets. For the purpose of oral therapeutic administration, the aforesaid compounds may be incorporated with excipients and used in the form of tablets, troches, capsules, elixirs, suspensions, syrups, wafers, chewing gums and the like. These preparations should contain at least 0.5% of active compound, but may be varied depending upon the particular form and may conveniently be between 4.0% to about 70% of the weight of the unit. The amount of xanthine in such composition is such that a suitable dosage will be obtained. Prefered compositions and preparations according to the present invention are prepared so that an oral dosage unit form contains between 1.0–300 mgs of active compound.

The tablets, pills, capsules, troches and the like may also contain the following ingredients: a binder such as microcrystalline cellulose, gum tragacanth or gelatin; and excipient such as starch or lactose, a disintegrating agent such as alginic acid, Primogel, corn starch and the like; a lubricant such as magnesium stearate or Sterotes; a glidant such as colloidal silicon dioxide; and a sweetening agent such as sucrose or saccharin or a flavoring agent such as peppermint, methyl salicylate, or orange flavoring may be added. When the dosage unit form is a capsule, it may contain, in addition to materials of the above type, a liquid carrier such as a fatty oil. Other dosage unit forms may contain other various materials which modify the physical form of the dosage unit, for example, as coatings. Thus tablets or pills may be coated with sugar, shellac, or other enteric coating agents. A syrup may contain, in addition to the active compounds, sucrose as a sweetening agent and certain preservatives, dyes and colorings and flavors. Materials used in preparing these various compositions should be pharmaceutically pure and non-toxic in the amounts used.

For the purposes of parenteral therapeutic administration, the xanthines may be incorporated into a solution or suspension. These preparations should contain at least 0.1% of the aforesaid compound, but may be varied between 0.5% and about 50% of the weight thereof. The amount of active compound in such compositions is such that a suitable dosage will be obtained. Prefered compositions and preparations according to the present invention are prepared so that a parenteral dosage unit contians between 0.5 to 100 mgs of the active compound.

The solutions or suspensions may also include the followiing components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in ampoules, disposable syringes or multiple dose vials made of glass or plastic.

We claim:

1. A method of enhancing host defense mechanisms against trauma which comprises administering to a host in need of defense mechanisms enhancement against trauma a defense mechanisms enhancing against trauma effective amount of a compound of the formula

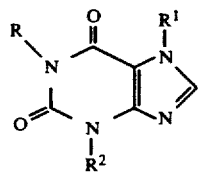

wherein R and R$^1$ are the same or different and are lower alkyl,

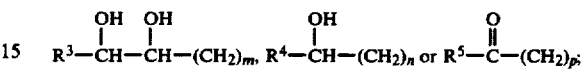

R$^2$ is lower alkyl; R$^3$ and R$^4$ are the same or different and are hydrogen or lower alkyl; R$^5$ is lower alkyl; and m, n and p are the same or different and are 2, 3 or 4, with the proviso that R, R$^1$ and R$^2$ are not simultaneously lower alkyl, or a pharmaceutically acceptable acid addition salt thereof.

2. A method according to claim 1 wherein R is

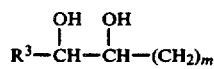

wherein R$^3$ and m are as abovedefined.

3. A method according to claim 1 wherein R is

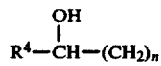

wherein R$^4$ and n are as abovedefined.

4. A method according to claim 1 wherein R is

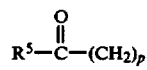

wherein R$^5$ and p are as abovedefined.

5. A method according to claim 1 wherein R$^1$ is

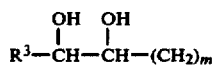

wherein R$^3$ and m are as abovedefined.

6. A method according to claim 1 wherein R$^1$ is

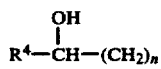

wherein R$^4$ and n are as abovedefined.

7. A method according to claim 1 wherein R$^1$ is

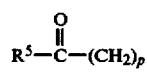

wherein R$^5$ and p are as abovedefined.

8. The method according to claim 1 wherein the compound is 1-(3,4-dihydroxybutyl)-3-methyl-7-(1-butyl)xanthine.

9. The method according to claim 2 wherein the compound is 1-(4,5-dihydroxypentyl)-3-methyl-7-(1-propyl)xanthine.

10. The method according to claim 2 wherein the compound is 1-(5,6-dihydroxyhexyl)-3-methyl-7-(1-propyl)xanthine.

11. The method according to claim 3 wherein the compound is 3,7-dimethyl-1-(5-hydroxyhexyl)xanthine.

12. The method according to claim 3 wherein the compound is 1-(5-hydroxyhexyl)-3-methyl-7-(1-propyl)xanthine.

13. The method according to claim 3 wherein the compound is 7-(1-butyl)-1-(5-hydroxyhexyl)-3-methylxanthine.

14. The method according to claim 3 wherein the compound is 3,7-diethyl-1-(5-hydroxyhexyl)xanthine.

15. The method according to claim 4 wherein the compound is 3-methyl-1-(5-oxohexyl)-7-(1-propyl)xanthine.

16. The method according to claim 4 wherein the compound is 7-ethyl-3-methyl-1-(5-oxohexyl)xanthine.

17. The method according to claim 4 wherein the compound is 7-(1-butyl)-3-methyl-1-(5-oxohexyl)xanthine.

18. The method according to claim 4 wherein the compound is 3-methyl-1-(4-oxopentyl)-7-(1-propyl)xanthine.

19. The method according to claim 4 wherein the compound is 3,7-diethyl-1-(5-oxohexyl)xanthine.

20. The method according to claim 5 wherein the compound is 3,7-dimethyl-1-(5-oxohexyl)xanthine.

21. The method according to claim 5 wherein the compound is 7-(3,4-dihydroxybutyl)-1,3-diethylxanthine.

22. The method according to claim 5 wherein the compound is 1-(1-butyl)-7-(5,6-dihydroxyhexyl)-3-methylxanthine.

23. The method according to claim 5 wherein the compound is 1,3-diethyl-7-(5,6-dihydroxyhexyl)xanthine.

24. The method according to claim 6 wherein the compound is 7-(5-hydroxyhexyl)-3-methyl-1-(1-propyl)xanthine.

25. The method according to claim 7 wherein the compound is 1-ethyl-3-methyl-7-(5-oxohexyl)xanthine.

26. A method of claim 1 wherein the trauma is associated with attack by a foreign body.

27. A method of claim 26 wherein the foreign body is a microorganism.

28. A method of claim 26 wherein the foreign body is a particle.

29. A method of claim 26 wherein the foreign body is a chemical agent.

30. A method of claim 27 wherein the microorganism is a virus.

31. The method of claim 27 wherein the microorganism is a bacteria.

32. A method of claim 27 wherein the microorganism is a fungus.

33. A method of claim 27 wherein the microorganism is a yeast.

34. A method of claim 27 wherein the microorganism is a parasite.

35. A method of claim 1 wherein the trauma is associated with physical injury.

36. A method of claim 35 wherein the physical injury is mechanical.

37. A method of claim 35 wherein the physical injury is thermal.

38. A method of claim 35 wherein the physical injury is electrical.

39. A method of claim 35 wherein the physical injury is radiational.

40. A method of claim 1 wherein the host is a mammal.

41. A method according to claim 1 wherein the enhancment of the host defense mechanism involves the increase of the motility of leukocytes towards the traumatic site.

42. A method of claim 41 wherein the motility is directed.

43. The method of claim 41 wherein the wherein the leukocyte is a granulocytic cell.

44. The method of claim 43 wherein the granulocytic cell is a neutrophil.

45. The method of claim 43 wherein the granulocytic cell is a basophil.

46. A method of claim 43 wherein the granulocytic cell is an eosinophil.

47. The method of claim 41 wherein the leukocyte is a monocyte.

48. A method of claim 47 wherein the monocyte is a macrophage.

49. The method of claim 47 wherein the monocyte is a lymphocyte.

50. The method of claim 49 wherein the lymphocyte is B-lymphocyte.

51. The method of claim 49 wherein the lymphocyte is T-lymphocyte.

52. A method of claim 1 wherein the effective amount of the compound is between about 0.10 mg/kg and about 10.0 mg/kg.

53. A method of claim 52 wherein the effective amount is about 1.0 mg/kg.

* * * * *

UNITED STATES PATENT AND TRADEMARK OFFICE
CERTIFICATE OF CORRECTION

PATENT NO. : 4,636,507

DATED : Jan. 13, 1987

INVENTOR(S) : Donald L. Kreutzer, William J. Novick, Jr. and Michael P. Sheetz

It is certified that error appears in the above-identified patent and that said Letters Patent is hereby corrected as shown below:

Column 1, line 28

"or $R^5-\overset{O}{\underset{}{C}}-(CH_2)_p$;" should be -- or $R^5-\overset{O}{\underset{}{C}}-(CH_2)_p$; $R^2$ is lower alkyl --

Column 2, line 15

"or $R^5-\overset{O}{\underset{}{C}}-(CH_2)_p$;" should be -- or $R^5-\overset{O}{\underset{}{C}}-(CH_2)_p$; $R^2$ is lower alkyl --

Column 7, line 48

"contians" should be -- contains --

Column 7, line 51

"followiing" should be -- following --

Signed and Sealed this

Twenty-eighth Day of June, 1988

Attest:

DONALD J. QUIGG

Attesting Officer

Commissioner of Patents and Trademarks